(12) United States Patent
Fang et al.

(10) Patent No.: US 7,565,246 B2
(45) Date of Patent: Jul. 21, 2009

(54) DETERMINATION OF GAS SATURATION RADIAL PROFILE FROM MULTI-FREQUENCY NMR DATA

(75) Inventors: Sheng Fang, Houston, TX (US); Songhua Chen, Katy, TX (US)

(73) Assignee: Baker Hughes Incorporated, Houston, TX (US)

( * ) Notice: Subject to any disclaimer, the term of this patent is extended or adjusted under 35 U.S.C. 154(b) by 0 days.

(21) Appl. No.: 11/689,887

(22) Filed: Mar. 22, 2007

(65) Prior Publication Data

US 2008/0234937 A1 Sep. 25, 2008

(51) Int. Cl.
*G01V 5/04* (2006.01)
(52) U.S. Cl. ........................................... 702/12
(58) Field of Classification Search ................. 702/12
See application file for complete search history.

(56) References Cited

U.S. PATENT DOCUMENTS

| | | | | |
|---|---|---|---|---|
| 5,059,907 | A * | 10/1991 | Sherman | 324/323 |
| 5,936,405 | A | 8/1999 | Prammer et al. | |
| 6,255,818 | B1 * | 7/2001 | Heaton et al. | 324/303 |
| 6,331,775 | B1 * | 12/2001 | Thern et al. | 324/303 |
| 6,703,832 | B2 * | 3/2004 | Heaton et al. | 324/303 |
| 6,954,066 | B2 * | 10/2005 | Siess et al. | 324/303 |
| 7,227,355 | B2 * | 6/2007 | Chen et al. | 324/303 |
| 7,301,338 | B2 * | 11/2007 | Gillen et al. | 324/303 |
| 2001/0054897 | A1 * | 12/2001 | Taicher et al. | 324/303 |
| 2004/0027122 | A1 * | 2/2004 | Heaton et al. | 324/303 |

FOREIGN PATENT DOCUMENTS

GB 2422198 A 12/2005

OTHER PUBLICATIONS

Fang S., Chen S., Tauk R., Fornange P., and Georgi D., 2004, Quantification of Hydrocarbon Saturation in Carboante Formations Using Simultaneous Inversion of Multiple NMR Echo Trains, paper 90569 presented at the SPE Annual Technical Conference and Exhibition held in Houston, Texas, USA Sep. 26-29.
S. Meiboom et al. "Modified Spin-Echo Method of Measuring Nuclear Relaxation Times" Rev. of Sci. Instr. vol. 29. No. 8. p. 688 (1958).
International Search Report for International Application No. PCT/US2008/057459. Mailed Jul. 8, 2008.
Written Opinion of the International Searching Authority for International Application No. PCT/US2008/057459. Mailed Jul. 8, 2008.

* cited by examiner

*Primary Examiner*—Michael P. Nghiem
*Assistant Examiner*—Cindy HienDieu Khuu
(74) *Attorney, Agent, or Firm*—Cantor Colburn LLP

(57) ABSTRACT

A method for determining fluid saturation in a formation at a plurality of radial depths near a wellbore, the method including: obtaining multi-frequency nuclear magnetic resonance (NMR) response data for the formation; and processing the data to determine simultaneously the fluid saturation at each radial depth. A computer program product is provided.

16 Claims, 10 Drawing Sheets

DETERMINATION OF GAS SATURATION RADIAL PROFILE FROM MULTI-FREQUENCY NMR DATA

BACKGROUND OF THE INVENTION

1. Field of the Invention

This invention relates to use of nuclear magnetic resonance (NMR) imaging techniques, and in particular, to use of multiple frequencies for determination of gas saturation radial profiles.

2. Description of the Related Art

Various instruments applying Nuclear Magnetic Resonance (NMR) imaging technology are useful for measuring certain petrophysical properties of earth formations. NMR well logging instruments typically include a magnet for polarizing nuclei in the earth formation in the vicinity of a wellbore. The polarizing typically occurs along a static magnetic field; at least one antenna is used for transmitting radio frequency ("RF") energy pulses into the formations, which manipulates spins for desired measurements. The magnitude of the RF energy emitted by the precessing nuclei and the rate at which the magnitude changes are related to certain petrophysical properties of interest in the earth formations.

A typical embodiment of an NMR logging instrument for characterization of geologic deposits includes a side-looking or "centralized" NMR logging instrument. Typically, the instrument operates using a gradient magnetic field and multiple frequencies $f$. One example of such an instrument is the MR Explorer$^{SM}$ provided by Baker Hughes, Incorporated of Houston Tex. (referred to as the "MREX instrument," the "logging instrument" or simply as the "instrument" herein).

There are several principal operating parameters in NMR well logging. These parameters should be optimized for efficient operation of an NMR well logging instrument. Such parameters include the logging speed (speed of motion of the instrument along the wellbore), the average and the peak power supplied to the instrument and transmitted as RF pulses, and the signal-to-noise ratio ("SNR"). Other parameters of interest include the vertical resolution of the instrument and the radial depth of investigation of the measurements made by the instrument within the formations surrounding the wellbore.

Physical parameters of particular interest to wellbore operators are the fractional volume of pore spaces in the earth formations ("porosity"), the texture of the rock and connectivity of the pore spaces, and the nature of the fluids contained in the pore spaces. Typical petroleum bearing earth formations contain water and hydrocarbon; some pores may be filled with water and others with hydrocarbons. Since hydrocarbons generally have different NMR relaxation properties than water, various NMR relaxometry techniques have been developed to qualitatively determine the nature of the fluids present in certain earth formations.

One method, for example, enables discriminating between gas and oil, and light oil and water. This method includes performing NMR spin-echo experiments using two different "wait times", $T_w$. The wait time $T_w$ is the delay between individual Carr-Purcell-Meiboom-Gill ("CPMG") spin echo measurement sequences. See S. Meiboom et al, Rev. of Sci. Instr. v. 29, p. 6881 (1958). Another technique, described in U.S. Pat. No. 5,498,960 issued to Vinegar et al, uses two different inter-echo spacing times, $T_e$, for CPMG sequences measured in a gradient magnetic field. Typically, the inter-echo spacing time $T_e$ is the time between rephasing radio frequency (RF) energy pulses applied to the logging instrument's antenna to "rephase" precessing nuclei which are influenced by the NMR survey. The rephasing RF pulses result in the "spin echoes" whose amplitude is measured. Gas, oil and water generally have different self-diffusivities, and these differences will be reflected in differences in the apparent transverse relaxation time $T_2$ calculated for an earth formation between CPMG sequences measured using different values of the inter-echo spacing time $T_e$. The technique described in the Vinegar et al. '960 patent for discriminating types of fluids in pore spaces of earth formations typically uses two values of the inter-echo spacing time $T_e$.

In addition to the multiple inter-echo spacing time $T_e$ and multiple wait time $T_w$ acquisitions, the use of multiple frequencies f in NMR measurements enhances aspects of formation evaluation. State of the art NMR logging instruments have a depth of investigation (DOI), (interchangeably referred to as a "radial depth") less than about five (5) inches deep into a formation. Thus, the sensitive volume is typically flushed or invaded by mud filtrate. The difference in the depth of investigation associated with different frequencies makes it possible to study the variation of invasion within the span of NMR sensitive volumes. Such variation may be more observable for the gas reservoir, because the mobility of the gas is highest among all reservoir fluid types. By processing frequency data separately, it is possible to observe variation in gas saturations should it occur. However, since NMR sensitive volume span is limited to few inches only, the variation in the flushed zone saturation is limited, and the consistency of the results processed with individual-frequency data may be compromised for high-noise data.

Invasion can be seen as a process of replacement of movable formation fluids by mud filtrates introduced by drilling of a well. For a well having water-based drilling mud, the hydrocarbon saturation becomes smaller in the invaded zone due to the invasion of the water-based mud filtrate. For a well having oil-based drilling mud, the hydrocarbon saturation in the invaded zone could be increased from the native oil saturation (such as the case where there is movable water) or relatively unchanged. Gas saturation, $S_g$, is always reduced or intact in the invaded zone when using drilling mud that is either one of water-based or oil-based. In order to account for the varying possibilities, it is necessary to simultaneously use all frequency data in the processing.

Therefore, what are needed are techniques for processing of data for multiple frequencies, where the processing techniques provide a determination of a gas saturation radial profile.

BRIEF SUMMARY OF THE INVENTION

Disclosed is a method for determining fluid saturation in a formation at a plurality of radial depths near a wellbore, the method including: obtaining multi-frequency nuclear magnetic resonance (NMR) response data for the formation; and processing the data to determine simultaneously the fluid saturation at each radial depth.

Also disclosed is a computer program product including machine readable instructions stored on machine readable media, the instructions for determining fluid saturation in a formation at a plurality of radial depths near a wellbore by: obtaining multi-frequency nuclear magnetic resonance (NMR) response data for the formation; and processing the data to determine simultaneously the fluid saturation at each radial depth.

BRIEF DESCRIPTION OF THE DRAWINGS

Referring now to the drawings wherein like elements are numbered alike in the several Figures.

DETAILED DESCRIPTION OF THE INVENTION

Multi-frequency NMR echo trains contain responses originating from fluids in pores of subterranean formations. Different response data may be realized for different radial positions, within distances as little as a few inches. The relaxation time distribution for the fluids inside the pores may be different due, at least in part, to an invasion process. The difference is particularly observable in the data from a gas well. Disclosed herein are techniques for determining fluid saturation from different frequency data. The techniques improve the sensitivity in detecting small variations of invasion by simultaneously processing all frequency data together and combining physical constraints.

Figure 1:
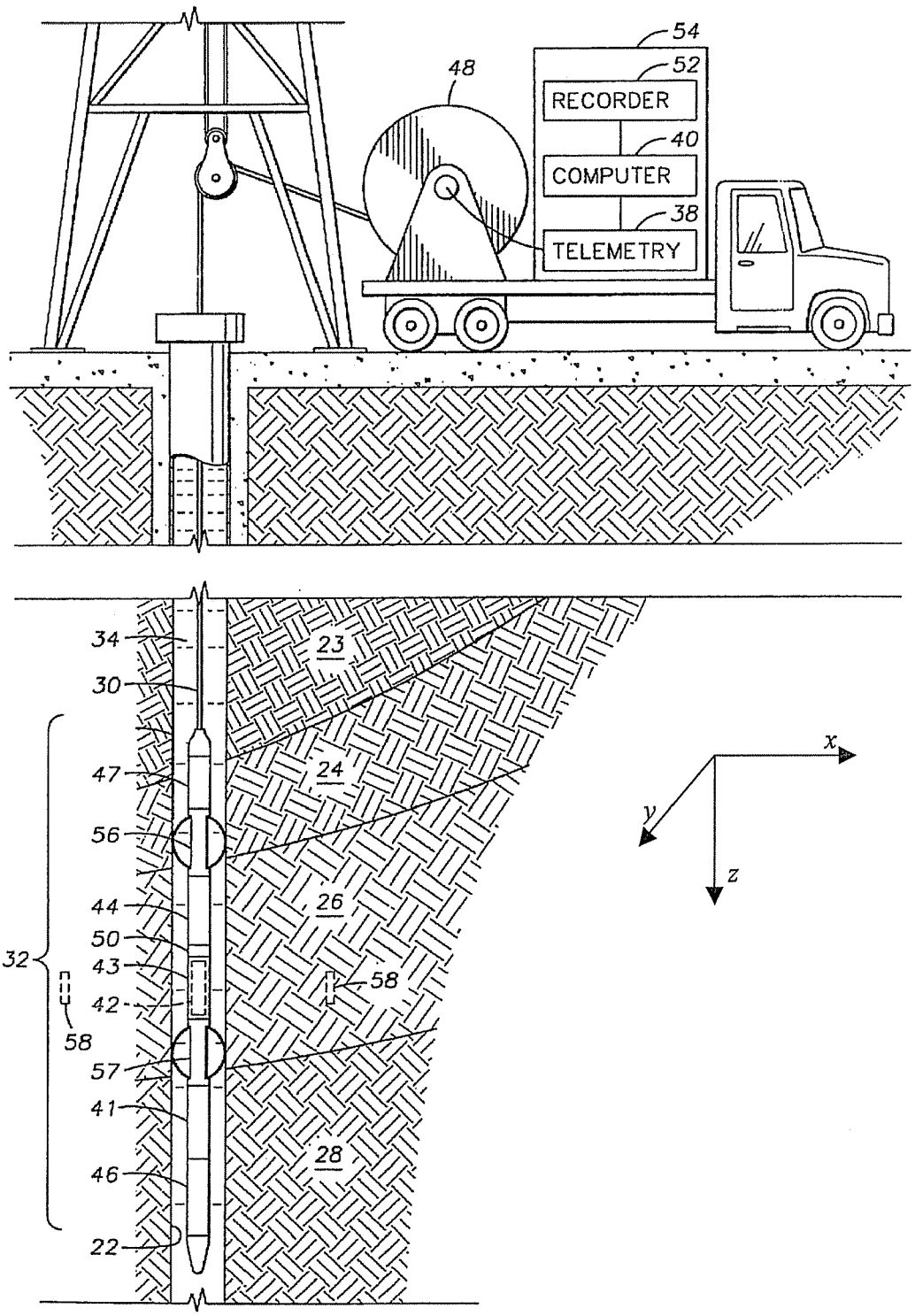
FIG. 1 depicts aspects of an NMR logging instrument in a wellbore.

FIG. 1 shows a well logging apparatus disposed in a wellbore 22 penetrating earth formations 23, 24, 26, 28 for making measurements of properties of the earth formations 23, 24, 26, 28. The wellbore 22 in FIG. 1 is typically filled with a fluid 34 known in the art as "drilling mud." A "sensitive volume," shown generally at 58 and having a either a cylindrical or a fraction of approximately cylindrical shape, is disposed in one of the earth formations, shown at 26. The sensitive volume 58 is a predetermined portion of the earth formations 26 in which nuclear magnetic resonance (NMR) measurements are made, as will be further explained.

Suitable NMR instruments for use in accordance with the teachings herein include, the MREX™ from Baker Hughes, Incorporated of Houston Tex., as well as the MRIL™, from Halliburton Corporation of Houston, Tex. The MREX™ generally includes a side-looking antenna and a gradient magnetic field for formation evaluation measurements and fluid analysis in almost any borehole environment regardless of borehole size, borehole deviation, or borehole conductivity. The side-looking design mitigates the effects of conducting drilling mud on the NMR data quality. The MREX™ generally uses static and pulsed radio-frequency magnetic fields to make downhole spin-echo magnetic resonance measurements. The basic principle of the MREX™ measurement is that of using a static magnetic field to polarize the protons in the formation fluids. One skilled in the art will recognize that these instruments, and other aspects of NMR instruments, as discussed herein or may be compatible, are exemplary and non-limiting.

In typical embodiments, the sensitive volume 58 includes materials such as would be found within a wellbore 22 including a mixture of liquids including water, salt water, drilling fluid, minerals, clay, mud, oil and formation fluids that are indigenous to the formations 23, 24, 26, 28, or introduced therein. NMR measurements may be used to determine a variety of formation properties and other aspects of interest.

It is recognized that certain fluids, such as drilling mud, may be of interest or present particular problems when performing measurements. In general, it is considered that drilling mud includes various components. For example, the drilling mud includes base fluid (typically of fresh water or brine, or oil or synthetic fluids), additives, and solid particles.

As used herein, the term "mud fluid" generally refers to the whole mud (the slurry that contains the solid particle and the liquid). The solid particles are blocked by the porous formation and forms a thin layer on the borehole wall (which is known as mud cake) and the base fluid, along with miscible additives, are "filtered" by and through the mud cake and invade into the formation, when borehole and formation pressure difference is greater than the capillary pressure of the mud cake. Thus, the invading fluid is often known as "mud filtrate." Further, the term "fluid" generally refers to liquid hydrocarbon, gas, water, mud filtrate, gas condensate and other fluids as known to those skilled in the art.

Turning again to FIG. 1, a string of logging instruments 32, typically including an NMR apparatus, is typically lowered into the wellbore 22 by a means of a cable 30. The cable 30 can be spooled and unspooled from a winch or drum 48. The instrument string 32 can be electrically connected to surface equipment 54 by an insulated electrical conductor (not shown separately in FIG. 1) forming part of the cable 30. The surface equipment 54 can include one part of a telemetry system 38 for communicating control signals and data to the instrument string 32 and computer 40. The computer may also include a data recorder 52 for recording measurements made by the apparatus and transmitted to the surface equipment 54. Typically, the computer includes a variety of input/output devices and other supporting devices to enhance the operation of the apparatus and estimations performed by use thereof.

An NMR probe 42 may be included in the instrument string 32. The configuration of an NMR measurement tool can be either centralized or decentralized. Shown in FIG. 1 is an example that the NMR tool is centered within the wellbore 22 by means of a top centralizer 56 and a bottom centralizer 57 attached to the instrument string 32 at axially spaced apart locations. The centralizers 56, 57 may be of types known in the art, such as bowsprings.

Circuitry for operating the NMR probe 42 can be located within an NMR electronics cartridge 44. The circuitry can be connected to the NMR probe 42 through a connector 50. The NMR probe 42 is typically located within a protective housing 43 which is designed to exclude the drilling mud 34 from the interior of the probe 42. The function of the probe 42 will be further explained.

Other well logging sensors (not shown separately for clarity of the illustration in FIG. 1) may form part of the instrument string 32. As shown in FIG. 1, one additional logging sensor 47 may be located above the NMR electronics cartridge 44. Other logging sensors, such as shown at 41 and 46 may be located within or below the bottom centralizer 57. Parts of the NMR electronics may be located within electronic cartridges which form part of other logging sensors. The locations of the other sensors 41, 46, 47 shown in FIG. 1 are a matter of convenience for the system designer and are merely exemplary.

Other aspects of the exemplary embodiment of the NMR probe 42 are provided in U.S. Pat. No. 5,712,566, entitled "Nuclear Magnetic Resonance Apparatus and Method," issued Jan. 27, 1998 to Taicher et al., and incorporated herein by reference in its entirety. Another non-limiting example is disclosed in U.S. Pat. No. 4,710,713, also issued to Taicher et al, and incorporated by reference herein in its entirety. It should be recognized that these embodiments of NMR instruments are exemplary only, and not limiting of the teachings herein.

The instrument string 32 is used to perform NMR measurements and collect NMR response data from within the wellbore 22.

The techniques disclosed herein provide a method for simultaneously determining gas saturations at different radial depths in the formation 26 near the wellbore 22 from NMR measurement data that includes measurements performed at different frequencies. In general, one embodiment of the technique calls for processing the measurement data using SIMET (Simultaneous Inversion of Multiple Echo Trains) without considering the variation of gas saturation $S_g$ from different frequency data; removing all non-movable fluids; removing fluid other than the gas and mud filtrate for a three-phase case (even though the effect from the fluid is typically small); calculating a geometric mean relaxation time $T_2$ for the gas; inverting partial porosities corresponding to the relaxation time $T_2$ bins for the movable fluid and to the single or several around the gas relaxation time $T_2$ geometric mean (where a monotonous variation constraint on gas saturation $S_g$ at different depths is used in the inversion algorithm); and calculating the gas saturations $S_g$ at different radial depths and output the results.

Figure 2:
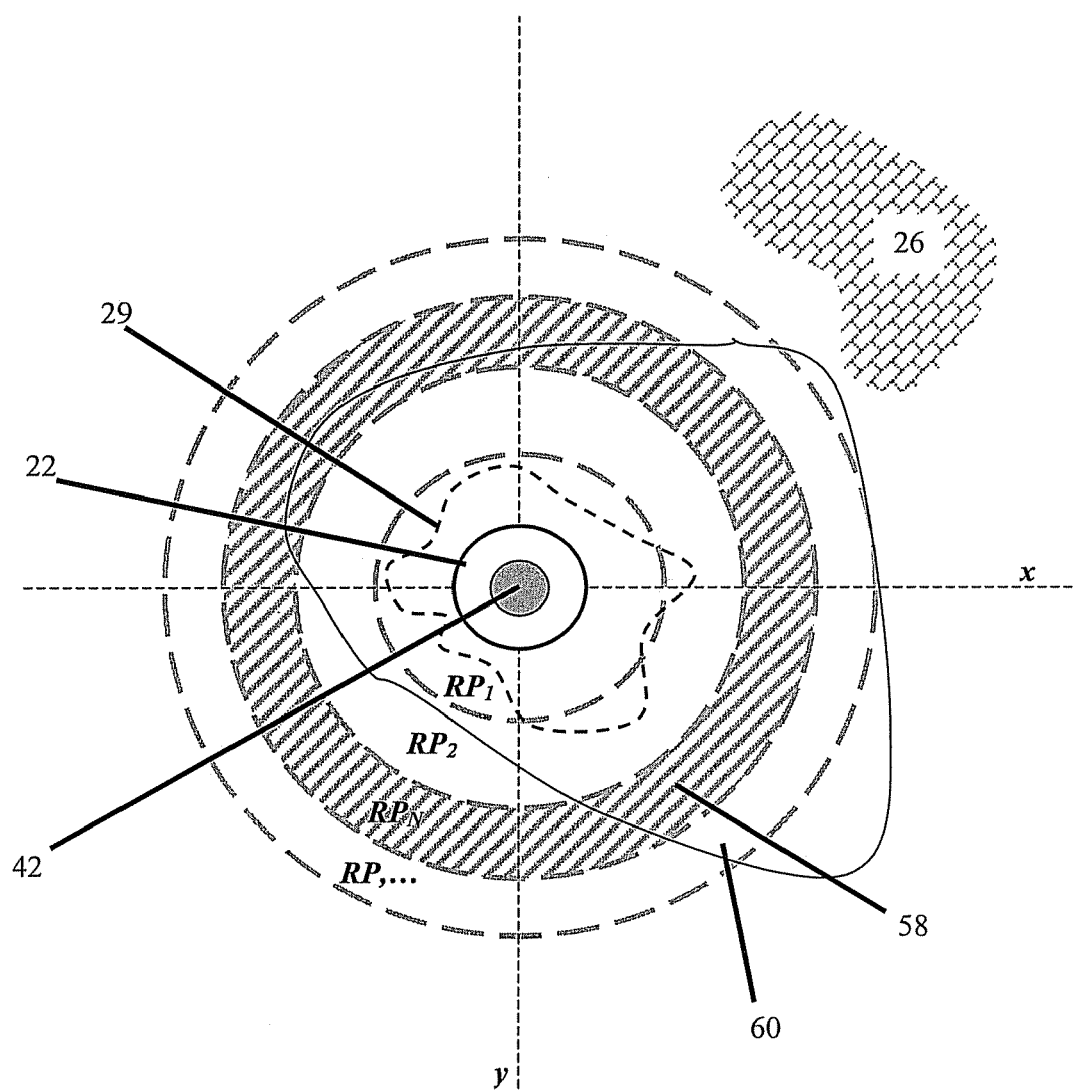
FIG. 2 depicts a radial profile where invasion exists within a gas deposition.

Multi-frequency NMR data contain responses from protons at different radial positions, $RP_x$, also referred to as a "radial depth." Consider the example provided in FIG. 2. In FIG. 2, the wellbore 22 is shown with the NMR probe 42 disposed therein. A series of radial positions $RP_1$, $RP_2$, ..., $RP_N$ are shown as concentrically surrounding the wellbore 22. Each radial position $RP_x$ occupies a portion of the surrounding formation 26, and represents a depth of investigation (DOI). The wellbore 22 traverses a gas deposition 60. A portion of the gas deposition 60 suffers from invasion, which is depicted as an invasion zone 29. Also as shown in FIG. 2, the sensitive volume 58 includes areas of the gas deposition 60, and the invasion zone 29 of the gas deposition 60.

Although the sensitive volume 58 is depicted as cylindrical or circular, this is not always the case. That is, the technique is not completely limited to cylindrical or a portion of the cylindrical shape. For example, the shape may be elliptical, or of some other shape. The shape typically does include a series of non-overlapping shells (i.e., radial depths) associated with different frequencies. For example, the sensitive volume 58 of the MREX™ instrument is not strictly circular. The sensitive volume does not have the same width of the ring (thinner on the sides so it is like a new crescent). In short, the sensitive volume 58 may include a variety of shapes and other geometric properties.

NMR data from the wellbore 22 typically includes complex data. For example, high frequency NMR signals may be affected more by invaded mud filtrate than the low frequency, deeper-reading signals. Therefore, it may be assumed that gas saturation $S_g$ derived from high frequency data will not be greater than gas saturation $S_g$ estimates determined from lower frequency data. An algorithm that takes account of all frequency data simultaneously may use this assumption advantageously.

A technique for determination of gas saturations at different radial positions $RP_x$ is provided for herein. This technique recognizes that gas is generally displaced by mud filtrate (water or oil). Further, this technique recognizes that while oil (or water) inside the formation may also be at least slightly displaced by the water (or oil) in the mud filtrate; the response from this change is negligible and thus is not considered.

Figure 3:
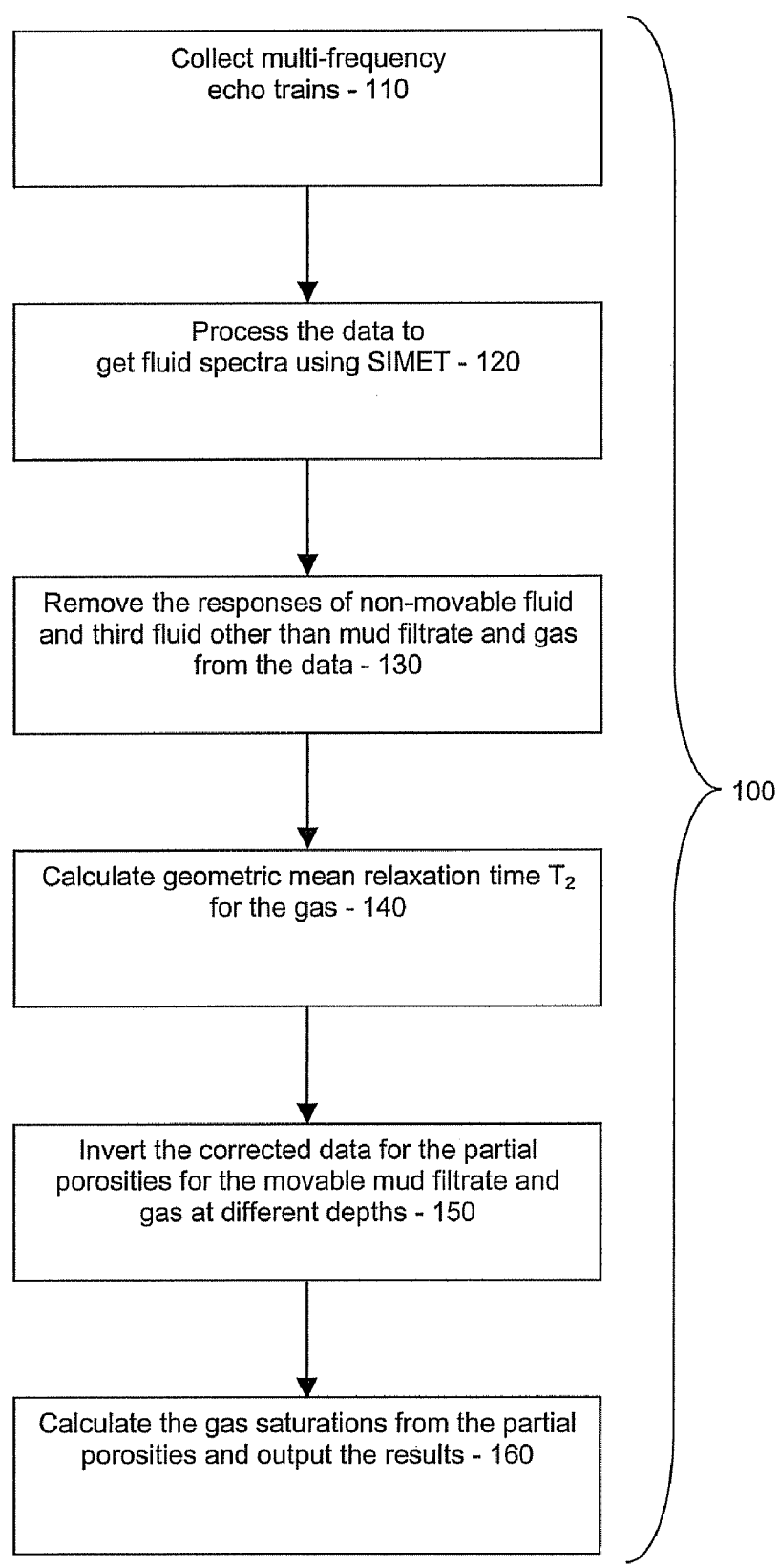
FIG. 3 depicts aspects of a procedure for determining gas saturations at different radial positions.

Referring now to FIG. 3, an exemplary algorithm 100 for determining a radial profile for gas saturation $S_g$ from NMR data is provided. In a first step 110, response data from multi-frequency NMR echo trains is obtained. In a second step 120, a non-movable fluid component in the gas deposition 60 is determined and then removed from the data. Accurate determination of the non-movable fluid component is provided as a result of Simultaneous Inversion of Multiple Echo Trains (SIMET) processing. SIMET is used to derive the spectra for different fluids assuming the gas deposition 60 has a generally similar appearance for each radial position $RP_x$. Although one skilled in the art might recognize that the assumption could cause some errors in a final solution, spectra for the non-movable fluids are adequately accurate for removal from the total responses. Also it is possible to determine the non-movable fluids by processing single frequency data (using less data) to avoid such an assumption. Porosity for the movable fluid and gas is also obtained in the second step 120 (for further use) by the SIMET processing. In a third step 130, response from non-movable fluid (and fluid other than the mud filtrate and gas) is removed.

In a third step 130, for a three-phase (i.e., a multi-phase) case, a third fluid in the formation (a fluid other than the mud filtrate and gas) is also assumed to have less effect due to the displacement by the mud filtrate. After response from interfering fluids (i.e., the third fluid) is removed from the response data, the remaining response in the response data is associated with movable mud filtrate and gas.

After the SIMET processing, if present, the non-movable fluids and the third fluid other than the movable fluid and gas can be removed. The geometric mean relaxation time $T_2$ for the movable mud filtrate ($T_{2mf}$) and the gas ($T_{2g}$) are calculated from the SIMET results. Also the total porosity ($\phi_{mv}$) for the movable mud filtrate fluid and gas is obtained. Since the gas has a pretty sharp spectrum, a single $T_{2g}$ or several bins around it are used. For the movable mud filtrate fluid, a single geometric mean relaxation time for the movable mud filtrate fluid, $T_{2mf}$, or several bins around geometric mean relaxation time $T_2$ can not provide the flexibility in describing the spectrum. Usually the bins that represent the movable part of the mud filtrate fluid are all used. If the mud filtrate fluid properties are known, such as the diffusivities D and ratios of longitudinal relaxation time $T_1$ over the transverse relaxation time $T_2$ for the fluid and gas, the response function, $A_i^j(t)$ for each bin can be represented by Eq. (1):

$$A_i^j(t) = HI_f \left(1 - e^{-\frac{Tw^j}{R_f T_{2i}}}\right) e^{-\frac{t}{T_{2i}}} e^{-\frac{(\gamma G^j Te^j)^2 D_f}{12} t} \tag{1}$$

where i represents $m_1, m_2, \ldots, m_M$, or g, whichever corresponds to the bins for fluid and the bin for gas; j represents different acquisition sequence of a specified wait-time Tw, inter-echo spacing Te and applied field gradient G; f represents m or g of the fluid or gas (respectively) which can be identified from the representation of i; HI represents a hydrogen index; D represents diffusivity; R represents the ratio of $T_1$ over $T_2$, and $\gamma$ represents the gyomagnetic ratio of hydrogen.

Once the response function, $A_i^j(t)$ has been determined, the echo trains are grouped by the gradient (G) values in an ascending order and represented as $j_k$(k=1, 2, ..., N), where N represents a number of frequencies. The partial porosities for the movable mud filtrate and single gas component are represented as $P_i^k$. Accordingly, the residual instrument responses after the removal of the responses from the non-movable fluids can be calculated according to Eq. (2):

$$M_{j_k}(t) = \sum_i A_i^{j_k} \cdot P_i^k. \tag{2}$$

Since the porosity $P_i^k$ can be reasonably assumed to be a constant at different radial positions, $RP_x$, Eq. (3) applies:

$$P_g^k = \phi_{mv} + \Delta\phi - \sum_{l=1}^{M} P_{ml}^k, \tag{3}$$

where $\phi_{mv}$ represents the total porosity for the movable mud filtrate and gas obtained from the SIMET results without considering the invasion 29 and M represents the number of bins for the movable mud filtrate. When the invasion process exists, the total porosity $\phi_{mv}$ is smaller than it should be due to the effects of a smaller gas hydrogen index. Thus, a correction term $\Delta\phi(>0)$ is introduced and inverted here for better accuracy. Substituting Eq. (3) into Eq. (2) and applying the correction term $\Delta\phi$ yields Eq. (4):

$$M_{j_k}(t) = \sum_i A_i^{j_k} \cdot P_i^k \tag{4}$$

$$= \sum_{l=1}^{M} A_{ml}^{j_k} \cdot P_{ml}^k + A_g^{j_k} \cdot P_g^k$$

$$= A_g^{j_k} \cdot \Delta\phi + \sum_{l=1}^{M} (A_{ml}^{j_k} - A_g^{j_k}) \cdot P_{ml}^k + A_g^{j_k} \cdot \phi_{mv}$$

Using matrix-vector notation, Eq. (4) can be written as Eq. (5):

$$A^k p^k = d^k \tag{5}$$

where $$A^k = [A_g^{j_k} \ (A_{m1}^{j_k} - A_g^{j_k}) \ (A_{m2}^{j_k} - A_g^{j_k}) \ \ldots \ (A_{mM}^{j_k} - A_g^{j_k})]; \tag{6}$$

$$p^k = [\Delta\phi \ P_{m1}^k \ P_{m2}^k \ \ldots \ P_{mM}^k]^T; \tag{7}$$

and $$d^k = [M_{j_k} - A_g^{j_k} \cdot \phi_{mv}]. \tag{8}$$

Based on the logics of invasion, the partial porosities $P_i^k$ corresponding to all bins of the mud filtrate for different frequencies f satisfy the relationship provided in Eq. (9):

$$P_{m1}^1 \leq P_{m1}^2 \leq \ldots \leq P_{m1}^N \tag{9}$$

$$P_{m2}^1 \leq P_{m2}^2 \leq \ldots \leq P_{m2}^N$$

$$\vdots$$

$$P_{mM}^1 \leq P_{mM}^2 \leq \ldots \leq P_{mM}^N$$

In order to implement the logic of Eq. (9) into the algorithm 100, an incremental notation for the partial porosities $P_i^k$ is provided as Eq. (10):

$$P_{m1}^2 = P_{m1}^1 + \Delta P_{m1}^1 \tag{10}$$

$$P_{m1}^3 = P_{m1}^1 + \Delta P_{m1}^1 + \Delta P_{m1}^2$$

$$\vdots$$

$$P_{m1}^N = P_{m1}^1 + \Delta P_{m1}^1 + \Delta P_{m1}^2 + \ldots + \Delta P_{m1}^{N-1}.$$

The same notations can be applied to $P_{m2}^k \ldots P_{mM}^k$. For all frequencies f, the unknowns can now be represented by the column vector provided in Eq. (11):

$$p = [\Delta\phi P_{m1}^1 \Delta P_{m1}^1 \ldots \Delta P_{m1}^{N-1} P_{m2}^1 \Delta P_{m2}^1 \ldots$$
$$\Delta P_{m2}^{N-1} \ldots P_{mM}^1 \Delta P_{mM}^1 \ldots \Delta P_{mM}^{N-1}]^T \tag{11}$$

Note that all elements in the vector p are nonnegative. The nonnegative constraints can be easily implemented into the inversion. The right hand side of Eq. (11) is the combination of all data that are calculated based on EQ. (8), for all frequencies, f. A typical arrangement is provided in Eq. (12):

$$d = \tag{12}$$

$$[(M_{j_1} - A_g^{j_1} \cdot \phi_{mv})^T \ (M_{j_2} - A_g^{j_2} \cdot \phi_{mv})^T \ \ldots \ (M_{j_N} - A_g^{j_N} \cdot \phi_{mv})^T]^T;$$

and a corresponding matrix is provided in Eq. (13):

$$A = [B_g \ B_{m1} \ B_{m2} \ \ldots \ B_{mM}]; \tag{13}$$

where

-continued $$B_g = \begin{bmatrix} A_g^{j1} \\ A_g^{j2} \\ \vdots \\ A_g^{jN} \end{bmatrix};$$ (14)

and $$B_{ml} = \begin{bmatrix} A_{ml}^{j1} - A_g^{j1} & & & \\ A_{ml}^{j2} - A_g^{j2} & A_{ml}^{j2} - A_g^{j2} & & \\ \vdots & \vdots & & \\ A_{ml}^{jN} - A_g^{jN} & A_{ml}^{jN} - A_g^{jN} & \ldots & A_{ml}^{jN} - A_g^{jN} \end{bmatrix},$$ (15)

$l = 1, 2, \ldots M.$

All of which resolves to a final equation to be solved, which is provided as Eq. (16):

$$Ap = d$$ (16);

where
$p \geq 0$.

Note that the size of matrix A is $NE_{total} \times (N \cdot M + 1)$, where $NE_{total}$ represents a total number of echoes for all echo trains. After obtaining the solution p and combining with the movable fluid porosity ($\phi_{mv}$) and the total porosity ($\phi_t$) from SIMET, the gas saturations at different radial positions $RP_x$ can be calculated by Eq. (17):

$$S_g^k = \frac{\phi_{mv} + \Delta\phi - \left[ p_{m1}^1 + p_{m2}^1 + \ldots + p_{mM}^1 + \sum_{l=1}^{k-1}(\Delta p_{m1}^l + \Delta p_{m2}^l + \ldots + \Delta p_{mM}^l) \right]}{\phi_t + \Delta\phi}$$ (17)

where
$k = 1, 2, \ldots, N$.

In a fourth step 140, a geometric mean for the relaxation time $T_2$ is calculated for the gas. Usually, the spectrum associated with gas is very sharp and can be represented by a single geometric mean, while the spectrum for movable mud filtrate fluid (water or oil) is more complicated. In this case, the spectrum for movable mud filtrate fluid is typically represented by all relaxation time $T_2$ bins. One bin (up to several bins) around the geometric mean for the relaxation time $T_2$ of the movable mud filtrate fluid may be used. The geometric mean(s) for the relaxation time $T_2$ are calculated from the SIMET results in the second step 120, after the removal of non-movable fluid and the third fluid. In a fifth step 150, calculation of the partial porosities corresponding to those bins for different frequency data and a correction term for the movable fluid porosity is determined by a linear inversion. Calculation of the partial porosities is constrained by aspects of the invasion. In a sixth step 160, the gas saturations for different frequency data are then calculated from the partial porosities and a corresponding porosity correction term. It is natural for one skilled in the art that the steps for the removal of non-movable fluids and the third fluid other than mud filtrate and gas are optional. All can be included in the inversion described above.

In order to validate the algorithm 100, two cases are presented. A first case considers a two-phase model with a gradually changed profile for the gas saturation $S_g$. A second case involves processing of a two-phase model that has no invasion. The responses are calculated for a typical acquisition sequence (where the response data is provided by twenty four (24) echo trains using six (6) frequencies).

For each case, five different noises (each noise having 100 levels) were added to synthetic data. The noise levels were based on noise characteristics of real measurements. The first four noise models were pure random noises of either zero, half, one time, or double the standard deviation of corresponding echo train. The last noise model used noise channel data. In both cases, the diffusivities for water and gas were taken as 5.2E-9 m²/s and 70.0E-9 m²/s. The ratios of the relaxation time $T_1$ over the relaxation time $T_2$ for water and gas were 2 and 1, respectively. The relaxation time $T_2$ bin position for gas was 3 sec and the hydrogen index was 1 for water and 0.5 for gas. The total porosity used was 25.7 pu in both cases.

Figure 4:
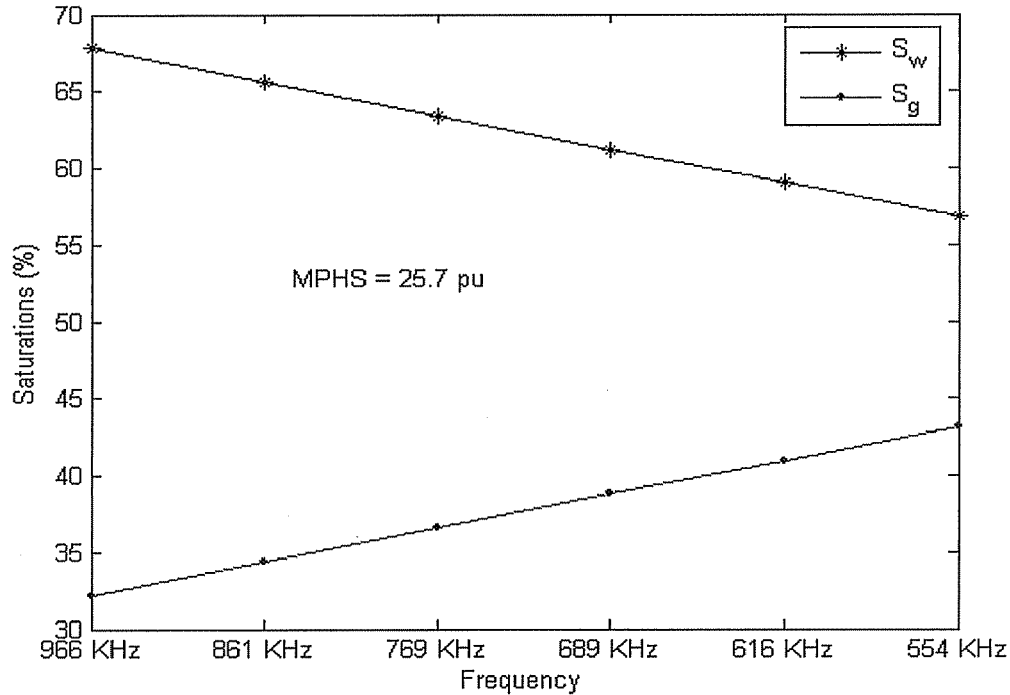
FIG. 4 illustrates variation of water and gas saturations determined at six different frequencies.
Figure 5:
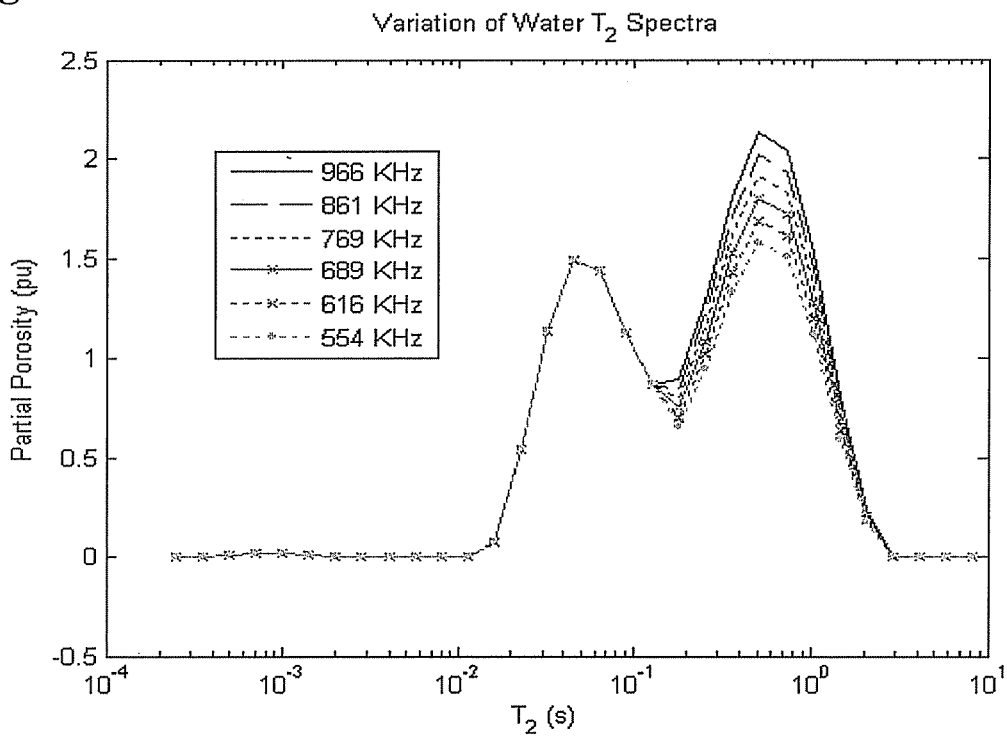
FIG. 5 illustrates variability of water relaxation time $T_2$ spectra for six different frequencies.
Figure 6:
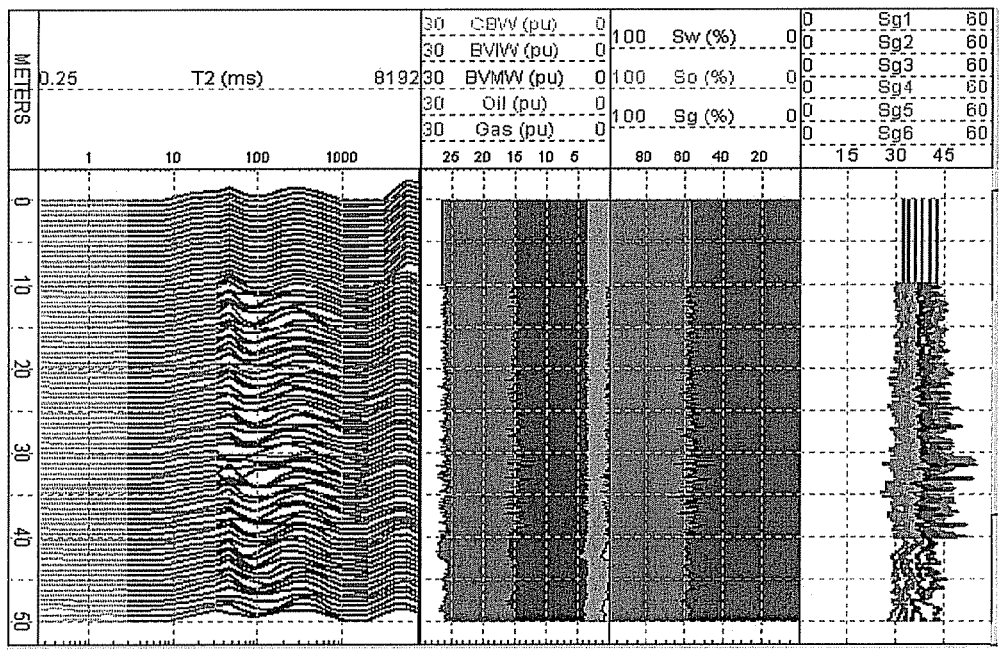
FIG. 6 depicts a user interface showing aspects of Simultaneous Inversion of Multiple Echo Trains (SIMET) results with consideration being given to an invasion process.
Figure 7:
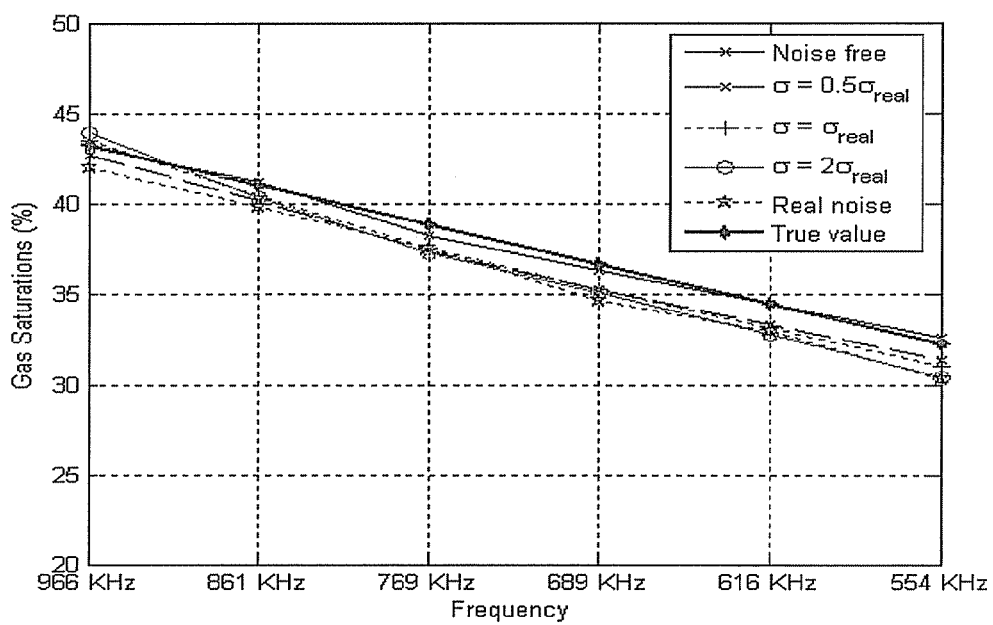
FIG. 7 provides a comparison of gas saturations for different noise models and at different frequencies against the true model.

In the case involving invasion, the gas saturation $S_g$ varied from about 32% to 43% (see FIG. 4). The correlating water relaxation time $T_2$ spectra at different frequencies (equivalent to different radial positions $RP_x$) are shown in FIG. 5. FIG. 6 depicts a user interface showing results of the SIMET inversion where consideration is given to the varied gas saturation $S_g$ and water saturation $S_w$. In FIG. 7, mean gas saturation $\bar{S}_g$ for 100 levels of five different noise models is compared to the true values provided. As shown, the gas saturation $S_g$ for different radial positions $RP_x$ can be determined within the error of about five percent for all five noise models. SIMET results (without consideration of the invasion process) are shown in FIG. 8.

Figure 8:
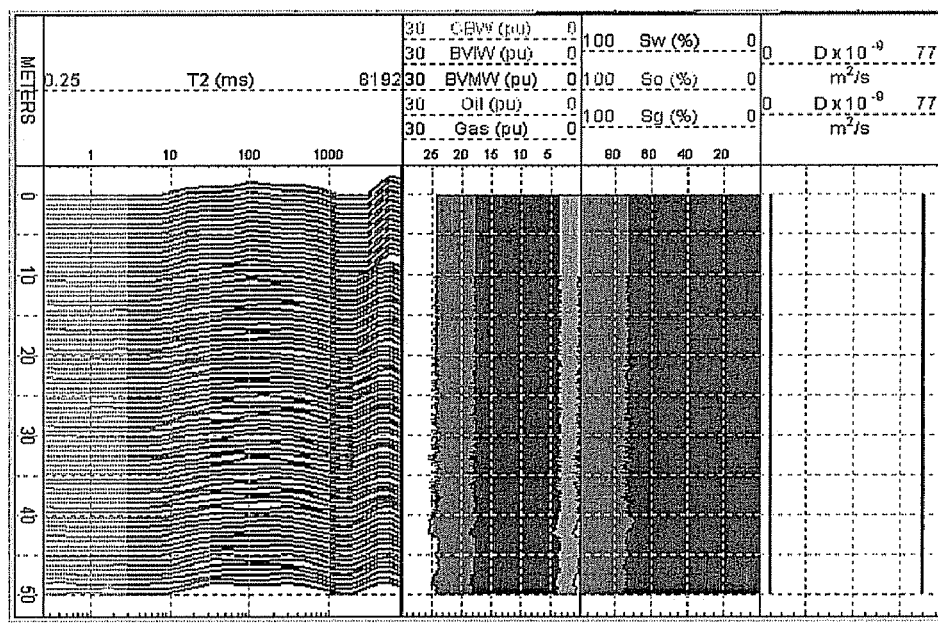
FIG. 8 depicts a user interface showing aspects of SIMET results without consideration being given to the invasion process.
Figure 9:
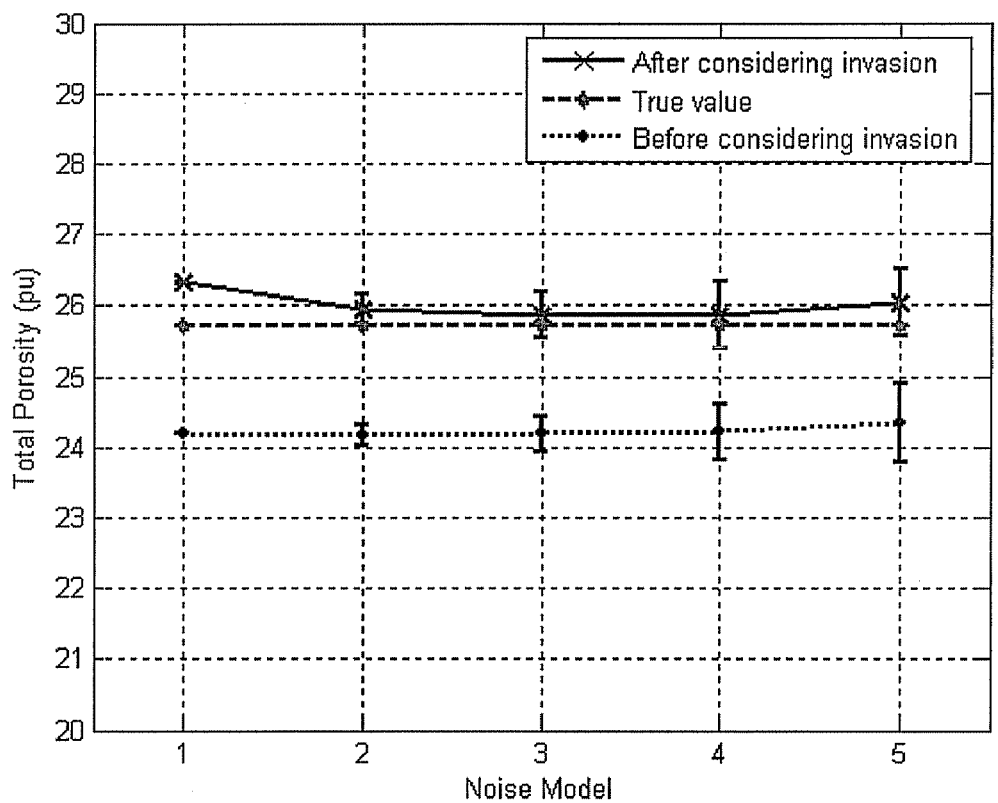
FIG. 9 provides a comparison of total porosities for different noise models before and after the consideration of the invasion process.

Two observations can be originated from FIG. 8: one is that the gas saturation $S_g$ (about 25%) is smaller than either one of the true values (32%-43%) for different frequencies; the other is that the total porosity is more than one pu smaller than the true one. Comparison of the total porosities with and without the consideration of the invasion process is shown in FIG. 9. With the consideration of the invasion process, the total porosity can be improved to an accuracy of 1 pu.

Figure 10:
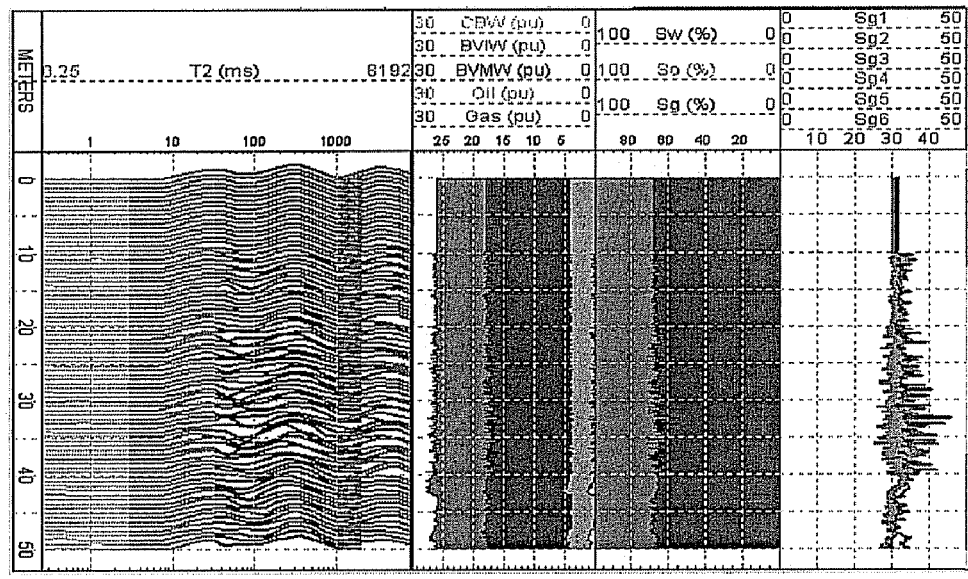
FIG. 10 depicts aspects of SIMET results with the consideration of the invasion process for a model without the invasion

In the case where no invasion occurs, the gas saturation $S_g$ is unchanged and kept 30% at all radial positions. All other parameters are the same as those used in the case 1. The purpose of testing this case is to see if the inversion creates some artifacts. FIG. 10 shows the results. It is observed that the consistent invasion can not be identified within an accuracy of about five percent based on gas saturation $S_g$ for different frequencies $f_x$. The noise does cause some variations on the determined gas saturation $S_g$. However, the variation is smaller where the noise is smaller, and can be controlled by various processing techniques. One example of a suitable technique is performing a running average of noise data during data processing.

Figure 11:
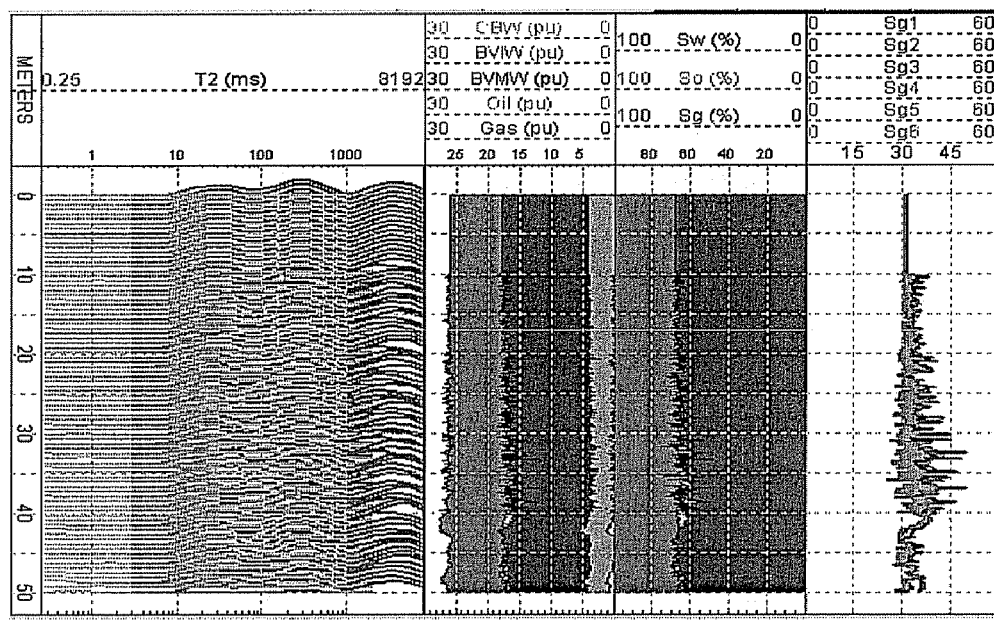
FIG. 11 depicts aspects of SIMET results with the consideration of the invasion process for a model without the invasion. Oil phase is considered in the SIMET FIG. 12 also depicts SIMET results with the consideration of the invasion process for a model without the invasion, where oil phase is considered in the SIMET and water based mud is assumed.
Figure 12:
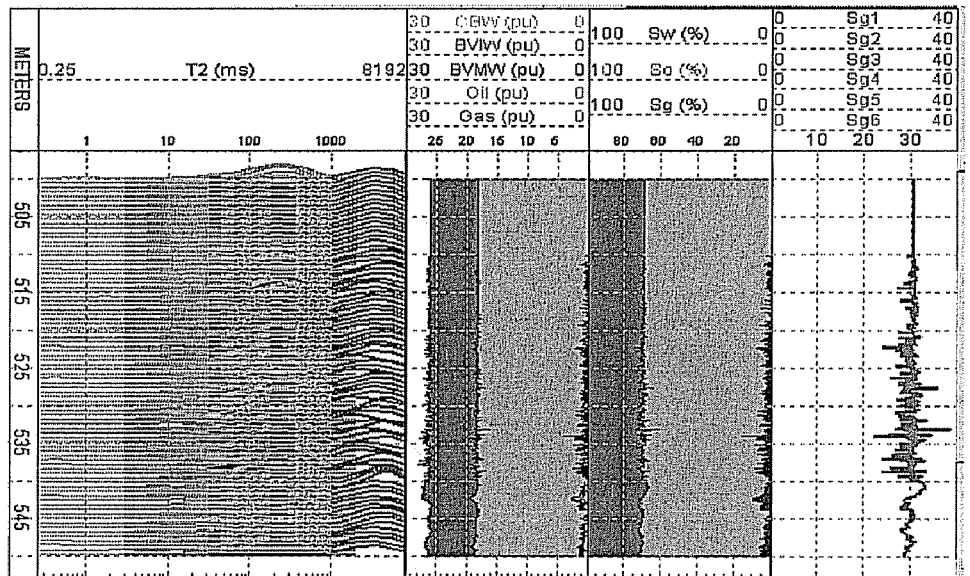
Figure 13:
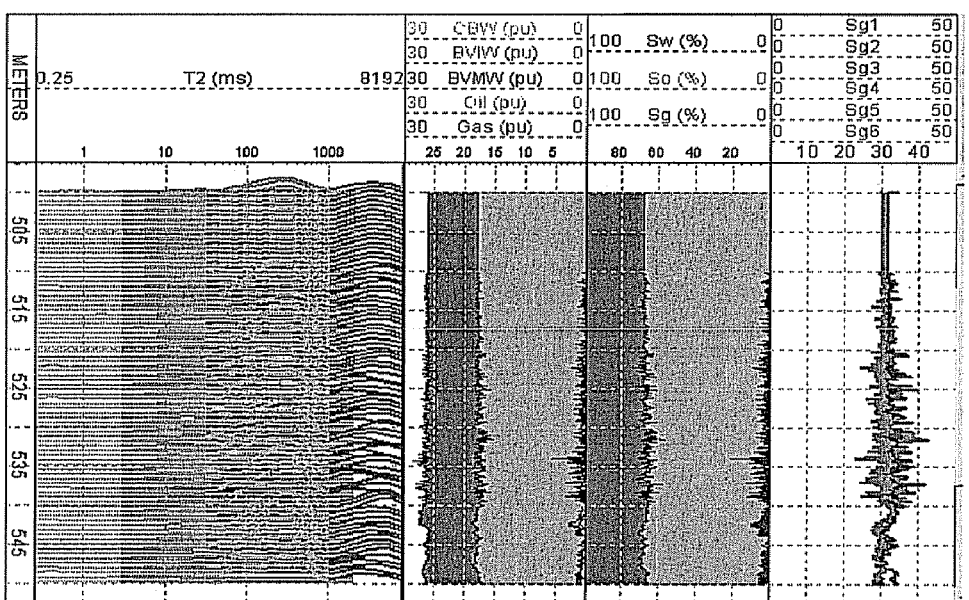
FIG. 13 shows SIMET results with consideration of the invasion process for a model without the invasion, and where oil phase is considered in the SIMET and oil based mud is assumed.

To further evaluate the stability of the algorithm 100, the oil phase is added in the inversion. The results are shown in FIG. 11. FIG. 11 shows that only a slight difference can be observed. FIGS. 12 and 13 show two additional examples that include oil spectrum in the model but processed with assumed water based mud or oil based mud, respectively. Again, the algorithm 100 does not create an artificial gas invasion profile.

Figure 14:
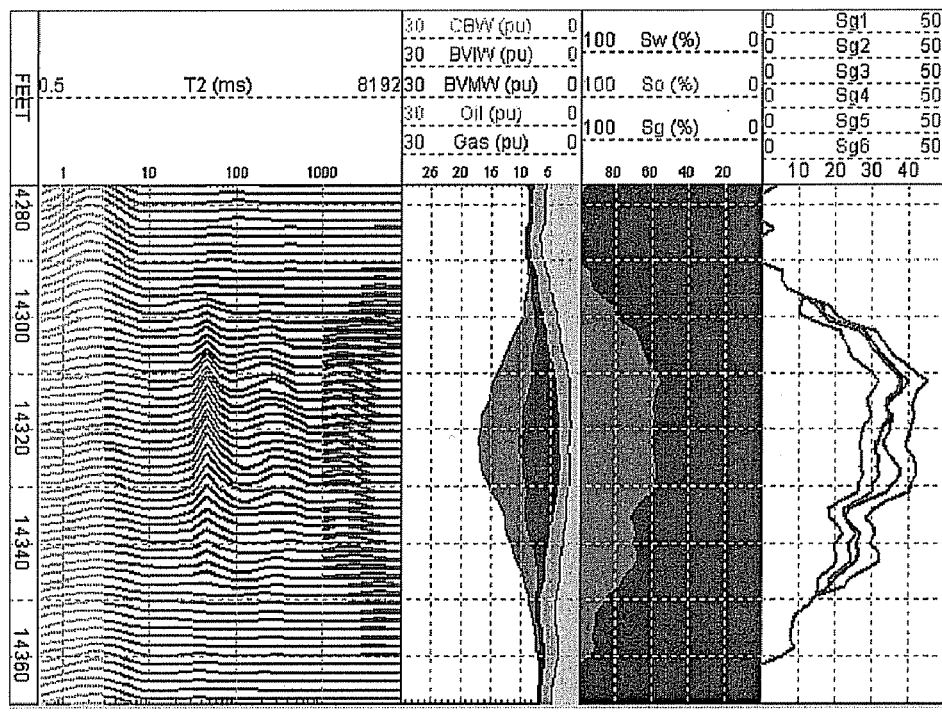
FIG. 14 shows SIMET results with the consideration of the invasion process, where the relaxation time $T_2$ spectra, porosities, and the saturations are all for the lowest frequency $f$.

By processing data from a wellbore 22 for a gas well, the invaded zone 29 with varied gas saturations $S_g$ can be identified and estimation of the total porosity can be improved. FIG. 14 shows such an example. To reduce the noise effects, the data were stacked using RA=16 (number of running average data points). It is recommended the data be stacked before using the algorithm 100.

Figure 15:
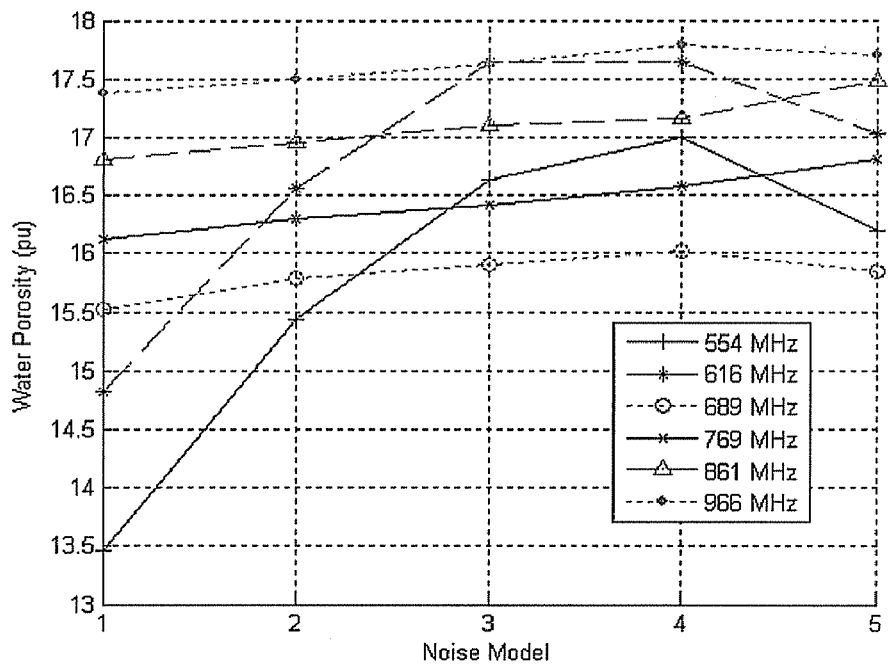
FIG. 15 shows water porosity results from processing of individual frequency data for five different noise models.
Figure 16:
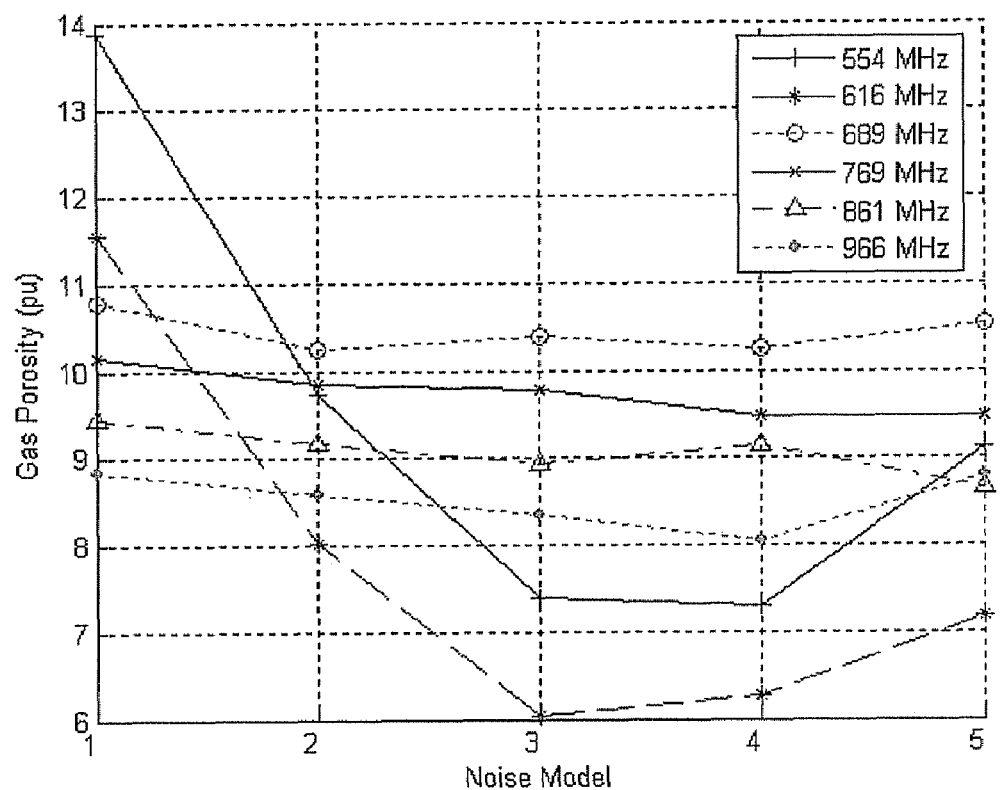
FIG. 16 depicts gas porosity results from processing individual frequency data using five different noise models.

Processing individual frequency data separately, the gas saturation $S_g$ at different depths may be obtained. However, the accuracy of determined gas saturation $S_g$ typically depends on the quality of data and the proper selection of acquisition sequences. Determined water and gas porosities at five different noise models are shown in FIGS. 15 and 16. These models are for PoroPerm and gas MREX acquisitions. From these two figures, it is observed that the results from the noise free data (noise model 1) clearly show the relative variation relationship among the solutions at different frequencies but the noise in the data destroy the relationship. In other words, the results from processing different frequency data separately could be distorted, even for the relative relationship. Increasing the level of running average may be helpful.

An invasion of mud filtrate in a gas well could cause the gas saturation $S_g$ to vary at different depths where investigation is performed. This variation can, sometime, be observed in the multi-frequency NMR acquisitions. Without considering this effect in the simultaneous inversion, the total porosity and the gas saturation $S_g$ would have some biases. By considering the invasion process in the simultaneous inversion, the gas saturation $S_g$ at varying depths of investigation can be well determined and the total porosity can be improved to a better accuracy.

In support of the teachings herein, various analysis components including at least one of a digital system and an analog system, the system having components such as a processor, storage media, memory, input, output, communications link (wired, wireless, optical or other), user interfaces, software programs, signal processors (digital or analog) and other such components (such as resistors, capacitors, inductors and others) may be had to provide for operation and analyses of the apparatus and methods disclosed herein. It is considered that these teachings may be implemented in conjunction with a set of computer executable instructions stored on a computer readable medium, comprising ROM, RAM, CD ROM, flash or any other computer readable medium, now known or unknown, that when executed cause a computer to implement the method of the present invention. These instructions may provide for equipment operation, control, data collection and analysis and other functions deemed relevant by a system designer, owner, user or other such personnel.

Further, various other components may be included and called upon for providing for aspects of the teachings herein. For example, at least one sample line, sample storage, sample chamber, sample exhaust, pump, piston, power supply (e.g., at least one of a generator, a remote supply and a battery), vacuum supply, pressure supply, refrigeration (i.e., cooling) unit or supply, heating component, motive force (such as a translational force, propulsional force or a rotational force), magnet, electromagnet; sensor, electrode, transmitter, receiver, transceiver, controller, optical unit, electrical unit and electromechanical unit may be included in support of the various aspects discussed herein.

Further still, the teachings herein may be suited for use in conjunction with other techniques known in the art. For example, it is considered that the teachings herein may be combinable or compatible with at least some other technologies or phenomena involving nuclear magnetic resonance (NMR), nuclear quadrupole resonance (NQR), seismic waves, acoustic waves, mineralogy, gravitation, conductivity, resistivity, permittivity, permeability, ionizing radiation and non-ionizing radiation as well as other technologies and phenomena.

One skilled in the art will recognize that the various components or technologies may provide certain necessary or beneficial functionality or features. Accordingly, these functions and features as may be needed in support of the appended claims and variations thereof, are recognized as being inherently included as a part of the teachings herein and a part of the invention disclosed.

While the invention has been described with reference to exemplary embodiments, it will be understood by those skilled in the art that various changes may be made and equivalents may be substituted for elements thereof without departing from the scope of the invention. In addition, many modifications may be made to adapt a particular instrument, situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method for determining fluid saturation in a formation at a plurality of radial depths near a wellbore, the method comprising:
   obtaining multi-frequency nuclear magnetic resonance (NMR) response data for the formation using a logging instrument; and
   processing the data to determine simultaneously the fluid saturation at each radial depth; wherein the processing comprises:
   processing the data to determine relaxation time spectra for fluids present in the formation;
   removing from the data the responses for relaxation time components corresponding to selected fluids;
   processing the data to determine the relaxation time spectra of mud filtrate and remaining formation fluid corresponding to each radial depth; and
   determining the fluid saturation.

2. The method as in claim 1, wherein the relaxation time comprises at least one of the longitudinal relaxation time, $T_1$, and the transverse relaxation time, $T_2$.

3. The method as in claim 1, wherein the processing comprises Simultaneous Inversion of Multiple Echo Trains (SIMET) processing.

4. The method as in claim 1, wherein the data comprises data for at least one of a plurality of frequencies and a plurality of echo-trains.

5. The method as in claim 1, wherein processing the data to determine the relaxation time spectra comprises implementing a physical constraint on a relationship among fluid saturations for each radial depth.

6. The method as in claim 5, wherein inverting comprises using an algorithm for monotonically increasing reservoir hydrocarbon saturation with the radial depth, where the invasion occurs.

7. The method as in claim 1, wherein the relaxation time for the fluid is not limited to a single relaxation time at each radial depth.

8. The method as in claim 2, wherein the fluid saturation is determined for at least one radial depth.

9. A computer program product comprising machine readable instructions stored on machine readable media, the instructions for determining fluid saturation in a formation at different radial depths near a wellbore, the instructions comprising instructions for:
   obtaining multi-frequency nuclear magnetic resonance (NMR) response data for the formation; and processing the data to determine simultaneously the fluid saturation at each radial depth wherein the processing comprises:

processing the data to determine relaxation time spectra for fluids present in the formation;

removing from the data the responses for relaxation time components corresponding to selected fluids;

processing the data to determine the relaxation time spectra of mud filtrate and remaining formation fluid corresponding to each radial depth; and determining the fluid saturation.

10. The computer program product as in claim 9, wherein the relaxation time comprises at least one of the longitudinal relaxation time, $T_1$, and the transverse relaxation time, $T_2$.

11. The computer program product as in claim 9, wherein the processing comprises Simultaneous Inversion of Multiple Echo Trains (SIMET) processing.

12. The computer program product as in claim 9, wherein the data comprises data for at least one of a plurality of frequencies and a plurality of echo-trains.

13. The computer program product as in claim 9, wherein processing the data to determine the relaxation time spectra comprises implementing a physical constraint on a relationship among fluid saturations for each radial depth.

14. The computer program product as in claim 9, wherein processing the data to determine the relaxation time spectra comprises using an algorithm for monotonically increasing reservoir hydrocarbon saturation with the radial depth, where the invasion occurs.

15. The computer program product as in claim 9, wherein the relaxation time for the fluid is not limited to a single relaxation time at each radial depth.

16. The computer program product as in claim 9, wherein the fluid saturation is determined for at least one radial depth.

* * * * *